(12) United States Patent
Mathews et al.

(10) Patent No.: US 9,206,452 B2
(45) Date of Patent: Dec. 8, 2015

(54) PLANT CELL CULTURE FOR PRODUCTION OF NATURAL PRODUCTS WITH REDUCED GLUCOSINOLATE CONTAMINATION

(71) Applicant: DIANAPLANTSCIENCES, INC., Portland, OR (US)

(72) Inventors: Helena V. Mathews, Portland, OR (US); Sung-Yong Yoon, Lake Oswego, OR (US); Mylavarapu Venkatramesh, Portland, OR (US)

( * ) Notice: Subject to any disclaimer, the term of this patent is extended or adjusted under 35 U.S.C. 154(b) by 124 days.

(21) Appl. No.: 14/062,452

(22) Filed: Oct. 24, 2013

(65) Prior Publication Data
US 2014/0051135 A1    Feb. 20, 2014

Related U.S. Application Data

(62) Division of application No. 13/140,381, filed as application No. PCT/US2009/068559 on Dec. 17, 2009, now Pat. No. 8,642,340.

(60) Provisional application No. 61/166,438, filed on Apr. 3, 2009, provisional application No. 61/138,884, filed on Dec. 18, 2008.

(51) Int. Cl.
| | | |
|---|---|---|
| *C12N 5/00* | (2006.01) | |
| *C12P 17/06* | (2006.01) | |
| *A01H 4/00* | (2006.01) | |

(52) U.S. Cl.
CPC .. *C12P 17/06* (2013.01); *A01H 4/00* (2013.01)

(58) Field of Classification Search
CPC .......... C12P 17/06; A01H 4/00; A01H 4/005; C12N 5/04; C12N 1/20; C12M 23/26; C12M 21/02
USPC ........................................................ 435/420
See application file for complete search history.

(56) References Cited

U.S. PATENT DOCUMENTS

| | | | |
|---|---|---|---|
| 5,866,762 A | 2/1999 | DeBonte et al. | |
| 7,250,559 B2 | 7/2007 | Quiros et al. | |
| 2008/0222754 A1 | 9/2008 | Bak et al. | |

FOREIGN PATENT DOCUMENTS

| | | | |
|---|---|---|---|
| JP | 2002/226730 | 8/2002 | |
| JP | 2002226730 | * 8/2002 | .............. C09B 61/00 |
| WO | 97/16559 | 5/1997 | |
| WO | 99/52345 | 10/1999 | |
| WO | 2004/089065 | 10/2004 | |

OTHER PUBLICATIONS

Giamoustaris et al. The effect of modifying the glucosinolate content of leaves of oilseed rape (*Brassica napus* ssp. *oleifera*) on its interaction with specialist and generalist pests. Ann. appl. Biol. (1995), 126:347-363.*

Durzan et al. Anthocyanin production in cell suspension cultures of Prunus cerasus cv. Vladimir. Adv. Hort. Sci. 5 (1991): 3-10.*
Rout, et al.—"In Vitro Selection and Biochemical Characterisation of Zinc and Manganese Adapted Callus Lines in *Brassica* spp."—Plant Science, 1999, vol. 137, pp. 89-100.
Hsieh, et al.—"A PII-like Protein in Arabidopsis: Putative role in nitrogen sensing"—Proc. Natl. Acad. Sci., Nov. 1998, vol. 95, pp. 13965-13970.
International Search Report and Written Opinion from International Application No. PCT/US2009/068559 mailed Sep. 8, 2010.
Palmer, M.V. et al., "Glucosinolate Content of Seedlings Tissue Cultures and Regenerant Plants of *Brassica juncea* (Indian Mustard)," Journal of Agricultural and Food Chemistry, vol. 35, No. 2, 1987, pp. 262-265.
Iqbal, M.C.M. et al., "Biosynthesis of Glucosinolates by Microspore Derived Embryoids and Plantlets in vitro of Brassica napus L.," Plant Science (Limerick), vol. 112, No. 1, 1995, pp. 107-115.
Halkier, B. et al., "Biology and Biochemistry of Glucosinolates," Annu. Rev. Plant Biol. 2006. 57; 303-333.
Supplementary European Search Report issued May 8, 2012, in European Application No. EP 09837935.7, filed Jul. 18, 2011.
Office Action dated Dec. 20, 2012, issued in U.S. Appl. No. 13/140,381, filed Jun. 16, 2011.
V. R. Shenoy, *Anthocyanins—Prospective Food Colours*, Current Science, vol. 63, No. 8 Apr. 25, 1995, pp. 575-579.
Michael Meyer et al., *Comparison of Glucosinolate Levels in Commercial Broccoli and Red Cabbage from Conventional and Ecological Farming*, Eur. Food Res Technol., vol. 226, 2008, pp. 1429-1437.
Dicosmo & Misawa, *Plant Cell Culture Secondary Metabolism, Chapter 2: Large-Scale Production of Secondary Metabolites by Plant Cell Cultures*, Boca Raton, Florida, CRC Press LLC., 1996, pp. 11-44.
Vaka Subba Reddy et al., *Ultraviolet-B-Responsive Anthocyanin Production in a Rice Cultivar is Associated with a Specific Phase of Phenylalanine Ammonia Lyase Biosynthesis*, Plant Physiol., vol. 105, 1994, pp. 1059-1066.
J. P. Nitsch et al., *Haploid Plants from Pollen Grains*, Science, vol. 163, 1969, pp. 85-87.

(Continued)

*Primary Examiner* — Annette Para
(74) *Attorney, Agent, or Firm* — Workman Nydegger

(57) ABSTRACT

Disclosed are methods for obtaining a natural product preparation with reduced glucosinolate contamination from a plant of *Brassicaceae*. The methods can include cultivating a plant callus from a plant capable of producing a desired natural product, selecting a callus with reduced glucosinolate production, and cultivating the selected callus in a liquid medium. The method can also include recovering the natural product from the culture. Also disclosed are methods for obtaining cabbage anthocyanin with reduced glucosinolate contamination. The methods can include cultivating a red cabbage plant callus with reduced glucosinolate production in a liquid medium to obtain a suspension culture and cultivating the suspension culture in a medium lacking a nitrogen source. The method can also include recovering the anthocyanin with reduced glucosinolate contamination from the culture. Finally, several specific low-glucosinolate cell lines are described.

20 Claims, 4 Drawing Sheets

(56) References Cited

OTHER PUBLICATIONS

Fred A. Mellon et al., *Intact Glucosinolate Analysis in Plant Extracts by Programmed Cone Voltage Electrospray LC/MS: Performance and Comparison with LC/MS/MS Methods*, Analytical Biochemistry, vol. 306, 2002, pp. 83-91.

Lijiang Song et al., *Purification of Major Glucosinolates from Brassicaceae Seeds and Preparation of Isothiocyanate and Amine Metabolites*, J. Sci. Food Agriculture, vol. 86, 2006, pp. 1271-1280.

Simone J. Rochfort et al., *Class Targeted Metabolomics: ESI Ion Trap Screening Methods for Glucosinolates Based on $MS^n$ Fragmentation*, Phytochemistry, vol. 69, 2008, pp. 1671-1679.

Notice of allowanced dated Jul. 19, 2013, issued in U.S. Appl. No. 13/140,381, filed Jun. 16, 2011.

International Preliminary Report dated Jun. 20, 2011, issued in PCT Application No. PCT/US2009/068559, filed Dec. 17, 2009.

\* cited by examiner

PLANT CELL CULTURE FOR PRODUCTION OF NATURAL PRODUCTS WITH REDUCED GLUCOSINOLATE CONTAMINATION

CROSS-REFERENCE TO RELATED APPLICATIONS

This application is a divisional of U.S. patent application Ser. No. 13/140,381, filed on Jun. 16, 2011, which issued as U.S. Pat. No. 8,642,340 on Aug. 4, 2007, which is a US Nationalization of PCT International Application No. PCT/US2009/068559, filed Dec. 17, 2009, which claims the benefit of U.S. Provisional Application No. 61/138,884, filed Dec. 18, 2008 and U.S. Provisional Application No. 61/166,438, filed Apr. 3, 2009, all of the foregoing applications being incorporated herein in their entirety by specific reference.

BACKGROUND OF THE INVENTION

1. The Field of the Invention

This disclosure relates to the field of plant cell culture and in particular, to the use of plant cell culture to produce natural products with reduced glucosinolate contamination.

2. The Relevant Technology

Synthetic food and cosmetic colorants are steadily being replaced by natural ones because of consumer preferences. Anthocyanins (polyphenolic pigments) are natural, water-soluble nontoxic pigments derived from fruits and vegetables, displaying a variety of colors from orange to blue. Because of their antioxidant properties, they may also have beneficial influence on human health (Shenoy, 1993, *Curr. Sci.* 64: 575-579). A drawback in the use of anthocyanins as food or cosmetic colorants is the presence of unpleasant taste and/or odor, particularly in anthocyanins extracted from red cabbage.

Anthocyanins are produced by chopping or crushing the fruit or vegetable and subsequent infusion of water acidified with a common food acid. This extract is then concentrated by non-chemical separation techniques. Pigment extracts from plant sources generally contain mixtures of different anthocyanin molecules, which vary by their level of hydroxylation, methylation and acylation. In some instances, such as anthocyanins extracted from red cabbage and radish, the extracts also contain undesirable components that contribute to unpleasant taste or odor of the extract. These factors can vary in the source plant from year to year, and are influenced by weather and environmental factors. Another challenge for the commercial production of anthocyanin pigments from plants is that harvest is often limited to once a year. This means a large volume of extract has to be prepared and stored for an extended period of time to supply the needs of the food industry throughout the year. Special storage conditions often have to be available due to the instability of anthocyanins. Additionally, the unpleasant taste and odor often develop after purification of the anthocyanin or other natural plant products from whole plants or plant tissues.

SUMMARY OF THE INVENTION

Plant cell culture technology provides an alternative source for the production and extraction of desirable plant natural products. The controlled environment of growing plant cells in defined nutrient media provides for year-round production and batch to batch consistency of product. Further, plant cell culture technology has the ability to select cell lines that have an enhanced ability to produce the desired compounds while undesirable compounds, such as those that impart undesirable odor or taste to the extracts, are not produced.

Disclosed herein are methods for obtaining natural product preparations (such as a *Brassicaceae* natural product, for example, a *Brassica* natural product) with reduced glucosinolate contamination and compositions including such natural products. Methods for producing a natural product preparation with reduced glucosinolate contamination include cultivating a plant callus (such as a *Brassicaceae* plant callus, for example, a *Brassica* plant callus), selecting a plant callus having reduced glucosinolate production (for example, less than about 5 μg total glucosinolate per gram fresh cell weight), and cultivating the selected callus in a suspension medium to obtain a suspension cell culture. The method can also include recovering the natural product (such as a *Brassicaceae* natural product, for example, a *Brassica* natural product) from the cell culture. In some examples, the natural product preparation is a natural pigment, such as anthocyanin.

Also disclosed herein are methods for producing cabbage anthocyanin with less than 100 mg/L glucosinolate contamination in the anthocyanin preparation. Methods for producing cabbage anthocyanin with less than 100 mg/L glucosinolate contamination in the anthocyanin preparation include cultivating a red cabbage plant callus with reduced glucosinolate production in a first suspension medium to obtain a suspension cell culture and growing the suspension cell culture in a second suspension medium. In some examples, the second suspension medium lacks a nitrogen source (for example, a medium lacking added ammonium and/or nitrate) and/or added phosphate (for example, a medium lacking added phosphate). The method can also include recovering the cabbage anthocyanin from the cell culture. In some embodiments, the suspension cell culture is grown in a second suspension medium that includes about 3-10% sucrose (for example, about 6% or 8% sucrose).

The foregoing and other features of the disclosure will become more apparent from the following detailed description, which proceeds with reference to the accompanying figures.

DETAILED DESCRIPTION

I. Introduction

Figure 1A:
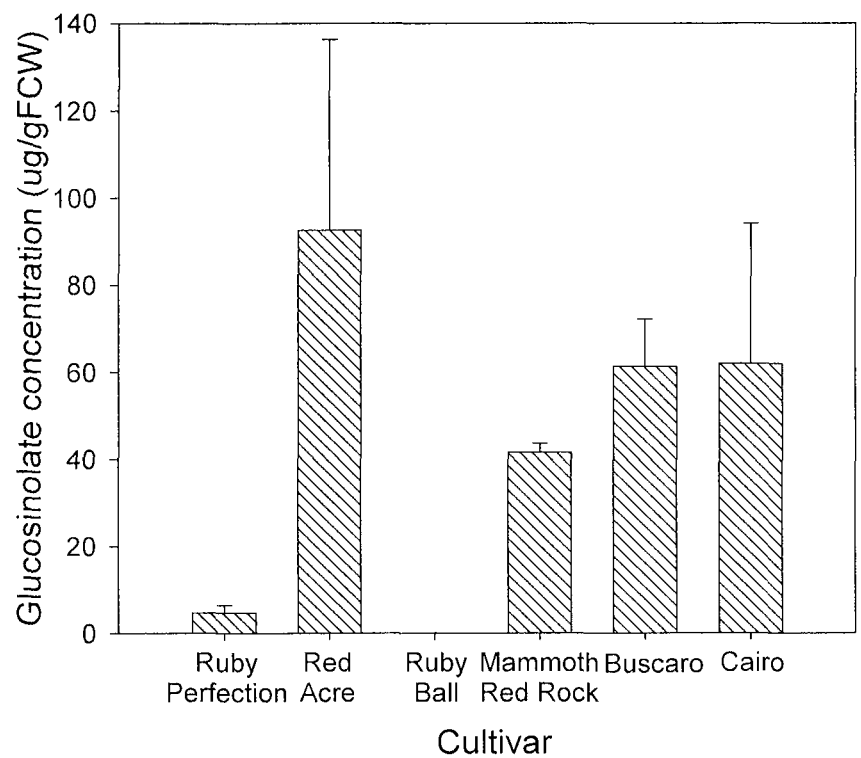
FIG. 1 is series of histograms showing total glucosinolate concentration of red cabbage cultivars in (FIG. 1A) stem-derived calli or (FIG. 1B) petiole-derived calli.

A viable cell culture system for the production of natural products (for example, anthocyanins) from *Brassica* has several potential advantages, including facilitating selective production of stable bioactive molecules and circumventing problems of uncertain, variable or seasonal supply. This involves development of a tissue culture system from a source plant and growing large scale plant suspension cultures similar to microbial fermentation systems. Growing plant cells in culture provides a highly controlled environment where nutrients can be manipulated to enhance cell growth and/or production of the desired natural product. Cell cultures are also amenable to treatments such as chemical or physical elicitation to increase production of desired compounds or to decrease production of undesirable compounds.

In the present disclosure, alteration of growth conditions allowed for the selection of red cabbage cell lines with reduced glucosinolate production. With the disclosed methods and described cell lines, anthocyanins with reduced glucosinolate content may be produced (as demonstrated in the Examples below). Additionally, culture of the cells in suspension medium lacking a nitrogen source increases anthocyanin production of the cells.

II. Overview of Several Embodiments

Disclosed herein are methods for obtaining natural product preparations (such as a *Brassicaceae* natural product, for example, a *Brassica* natural product) with reduced glucosinolate contamination and compositions including such natural products. In one embodiment, methods for producing the natural product with reduced glucosinolate contamination can include cultivating a plant callus (such as a *Brassicaceae* plant callus, for example, a *Brassica* plant callus) from a plant (such as a callus obtained from a cotyledon, root, hypocotyl, shoot tip, stem, leaf, or epidermal peel), selecting a plant callus with reduced glucosinolate production, and cultivating the selected callus in a suspension medium to obtain a suspension cell culture capable of producing a natural product with reduced glucosinolate contamination. In some particular examples, the plant callus with reduced glucosinolate production is produced by inducing the formation of the plant callus through in vitro culture in an induction medium. The method can also include recovering the natural product with reduced glucosinolate contamination from the culture.

In one embodiment, the plant callus (such as a *Brassicaceae* plant callus, for example, a *Brassica* plant callus) with reduced glucosinolate production contains less than 5 µg of total glucosinolate per gram fresh cell weight (FCW).

Also disclosed are methods for obtaining cabbage anthocyanins with less than 100 mg/L glucosinolate contamination in the anthocyanin preparation. Methods for producing cabbage anthocyanin with less than 100 mg/L glucosinolate contamination include cultivating a red cabbage plant callus (for example a callus from red cabbage Ruby Perfection, Red Acre, Ruby Ball, Mammoth Red Rock, Buscaro, or Cairo cultivar) with reduced glucosinolate production in a first suspension medium to obtain a suspension cell culture and growing the suspension cell culture in a second suspension medium (for example, a second suspension medium lacking a nitrogen source and/or phosphate). In some embodiments, the suspension cell culture is grown in a second suspension medium lacking a nitrogen source that also includes about 3-10% sucrose (for example about 4-8% sucrose, such as about 6% or 8% sucrose). In other embodiments, the suspension cell culture is grown in a second suspension medium that includes about 3-6% sucrose. The method can further include recovering the anthocyanin pigments from the cell culture.

Also provided are specific cell lines that are potentially low in glucosinolate production.

III. Abbreviations and Terms

A. Abbreviations 2,4-D: 2,4-dichlorophenoxyacetic acid
BA: 6-benzylaminopurine
ES: electrospray
FCW: fresh cell weight
LC-MS: liquid chromatography-mass spectrometry
MS: Murashige and Skoog vitamins or salts
NAA: α-naphthaleneacetic acid
NN: Nitsch & Nitsch vitamins
PCV: packed cell volume
PDA: photo diode array
RI: refractive index B. Terms In order to facilitate review of the various embodiments of the disclosure, the following explanations of specific terms are provided:

Anthocyanins: A group of water-soluble flavonoids that impart pink/red to purple color to leaves and other organs of plants. Common anthocyanins include derivatives of cyanidin, delphinidin, malvidin and pelargonidin. In an example, anthocyanin pigments are pigments formed after cultivation of a *Brassica* plant callus having reduced glucosinolate in a liquid medium (such as a medium lacking a nitrogen source).

*Brassica*: A genus of plants in the mustard family (*Brassicaceae*), which are sometimes known collectively as cabbages or mustards. Crops from this genus are sometimes called cole crops.

Species of the genus *Brassica* include, but are not limited to, *B. carinata* (Abyssinian mustard or Abyssinian cabbage), *B. elongata* (elongated mustard), *B. fruticulosa* (Mediterranean Cabbage), *B. juncea* (such as Indian mustard, brown and leaf mustards, Sarepta mustard), *B. napus* (such as rapeseed, canola, rutabaga), *B. nigra* (black mustard), *B. oleracea* (such as kale, cabbage, broccoli, cauliflower, Brussels sprouts), *B. rapa* (syn *B. campestris*) (such as Chinese cabbage, turnip, rapini), and *B. rupestris* (brown mustard). In particular examples, contemplated *Brassica* plants are *B. oleracea*, for example *B. oleraceae* var. *capitata* f. *rubra* (such as cultivars Ruby Perfection, Red Acre, Ruby Ball, Mammoth Red Rock, Buscaro, and Cairo).

*Brassicaceae*: Family of plants known as the mustard family or cabbage family (also known as Cruciferae or crucifers). Genera included in *Brassicaceae* include *Brassica, Raphanus, Armoracia, Matthiola, Arabidopsis*, and *Alyssum*. Members of *Brassicaceae* produce glucosinolate compounds. The family includes numerous economically significant plants, including food crops (such as cabbage, broccoli, cauliflower, turnip, rapeseed, canola, mustard, radish, horseradish, Brussels sprouts, kale, and rutabaga) and the model genetic organism *Arabidopsis thaliana*.

Callus: A mass of undifferentiated cells. A plant cell callus consists of somatic undifferentiated cells from a subject plant, such as an adult subject plant or a plant part including plant embryo. In an example, a callus (such as a red cabbage callus) has reduced glucosinolate content.

Contamination: Presence of an undesired component in a preparation. In one example "glucosinolate contamination" includes the presence of a glucosinolate in a natural product preparation from a plant of *Brassicaceae*, when glucosinolate (such as total glucosinolates or one or more particular glucosinolate) is present at a level that produces an unpleasant taste and/or odor (for example glucosinolate greater than about 5 µg/g fresh cell weight in a plant callus or greater than about 100 mg/L in a natural product preparation).

Control: A "control" refers to a sample or standard used for comparison with an experimental sample. In some embodiments, the control is a sample obtained from a plant or plant callus that has not been selected for reduced glucosinolate production (such as a callus induced on medium that does not include 2,4-dichlorophenoxyacetic acid, α-naphthaleneacetic acid, and/or 6-benzylaminopurine). In additional embodiments, the control is an anthocyanin preparation produced from a plant callus or a suspension culture that has not been selected for reduced glucosinolate production. In some examples, the control may be from the plant or the plant callus from which the callus selected for reduced glucosinolate production was derived. In other embodiments, the control is a historical control or standard reference value or range of values (such as a previously tested control sample, such as a plant or plant callus that has not been selected for reduced glucosinolate production or an anthocyanin preparation produced from a plant callus or suspension culture that has not been selected for reduced glucosinolate production).

Glucosinolate: A class of organic compounds containing sulfur and nitrogen, derived from glucose and an amino acid. Glucosinolates are produced by almost all plants of the order Brassicales (including the family *Brassicaceae*) and are responsible for the bitter or "sharp" taste of foods including mustard, radish, cabbage, Brussels sprouts, kale, cauliflower, broccoli, and turnip. Compounds derived from glucosinolates are natural defense compounds of plants against insects and herbivores.

In some examples, the glucosinolates include glucosinolates produced by *Brassica* plants, such as glucosinolates produced by red cabbage (for example, glucoiberin (3-methoxysulfinylpropyl-glucosinolate), progoitrin ((2R)-hydroxy-3-butenyl-glucosinolate), sinigrin (2-propenyl-glucosinolate), glucoraphanin (4-methylsulfinylbutyl-glucosinlate), gluconapin (3-butenyl-glucosinolate), 4-hydroxy-glucobrassicin (4-hydroxy-3-indolymethyl-glucosinolate), glucotropaeolin (benzyl-glucosinolate), glucoerucin (4-methylthiobutyl-glucosinolate), glucobrassicin (3-indolmethyl-glucosinolate), 4-methoxy-glucobrassicin (4-methoxy-3-indolymethyl-glucosinolate), and neo-glucobrassicin(1-methoxy-3-indolmethyl-glucosinolate). See, e.g., Meyer and Adam, *Eur Food Res Technol.* 226:1429-1437, 2008.

Natural product: A chemical compound or substance produced by a living organism or cells (such as cells in culture) that usually has a pharmacological or biological activity (such as for use as a drug or in drug discovery or design) or other useful properties (such as for a food additive). In an example, a natural product is anthocyanin, such as anthocyanin produced by a *Brassicaceae* plant (for example, a *Brassica* plant, such as red cabbage) or *Brassicaceae* cells in culture (such as a *Brassica* callus or a suspension culture, for example a red cabbage callus or suspension culture).

A natural product (such as anthocyanin) produced from a plant or cells from the family *Brassicaceae* may contain undesirable contaminants (such as glucosinolates) which result in unpleasant taste or odor. In an example, the natural product (such as a natural product extract) is produced from a *Brassicaceae* plant callus with reduced glucosinolate production, resulting in a natural product with reduced glucosinolate contamination.

Nitrogen source: A compound that provides nitrogen to a plant or plant cell culture (such as a callus or suspension culture). Nitrogen sources include ammonium (such as ammonium nitrate or ammonium sulfate) and nitrate (such as ammonium nitrate, potassium nitrate, or calcium nitrate). A growth medium that lacks a nitrogen source is a medium that does not include an added nitrogen source, such as added nitrogen in the form of ammonium or nitrate, such as medium that contains less than about 100 µM ammonium and/or nitrate (such as less than about 1 µM, less than about 100 nM, less than about 1 nM, or less than about 0.1 nM ammonium and/or nitrate), or medium that does not contain detectable levels of ammonium and/or nitrate, for example by mass spectrometry.

pH: A measure of the acidity or alkalinity of a solution. An aqueous solution at 25° C. with a pH less than seven is acidic, while a solution with a pH greater than seven is considered basic (alkaline). In an example, an acidic pH is less than five, such as between one and three.

Plant cell: Any cell derived from a plant, including cells from undifferentiated tissue (e.g., callus) as well as plant seeds, pollen, propagules and embryos. Plant cells can be obtained from any plant organ or tissue and cultures prepared therefrom.

Plant part: Any plant organ or tissue, including, without limitation, seeds, embryos, meristematic regions, callus tissue, leaves, roots, shoots, stems, gametophytes, sporophytes, pollen, and microspores.

Red cabbage: The red cabbage (e.g., *Brassica oleracea* var. *capitata* f. *rubra*) is a variety of cabbage, also known as Red Kraut or Blue Kraut after preparation (e.g., the blue color is formed after cooking) In one example, the red cabbage is cultivar Ruby Ball.

Reduced: Less or smaller, as in number, amount, level, concentration, or intensity. In one example, reduced glucosinolate production (such as by a plant callus) is a decreased amount of glucosinolate (such as concentration of glucosinolate or a ratio of anthocyanin to glucosinolate) as compared with a control plant callus. In another example, reduced glucosinolate contamination is a decreased amount of glucosinolate (such as concentration of glucosinolate or a ratio of anthocyanin to glucosinolate) in a preparation as compared to a control preparation.

Suspension culture: The growth of cells separate from the organism. This is typically facilitated via use of a liquid medium (a "suspension medium"). Suspension culture can refer to the growth of cells in liquid nutrient media.

Tissue culture: Tissue culture commonly refers to the culture of cells and tissues on solid nutrient media.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means including A, or B, or A and B.

It is further to be understood that all base sizes or amino acid sizes, and all molecular weight or molecular mass values, given for nucleic acids or polypeptides or other molecules are approximate, and are provided for descriptive purposes, unless otherwise indicated. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., DiCosmo, F. and Misawa, M. (Eds.) *Plant Cell Culture Secondary Metabolism,* 1996, CRC Press, Boca Raton, 232 pp; Payne, G. F., Bringi, V., Prince, C. L., and Shuler, M. L. *Plant cell and tissue culture in liquid systems,* 1992, John Wiley & Sons, Inc, New York, 346 pp; Gamborg, O. L. and Phillips, G. C. (Eds.). *Plant cell, tissue and organ culture: Fundamental methods,* 1995, Springer-Verlag Berlin Heidelberg, 307 pp; Fu, T-J, Singh, G., and Curtis, W. R. (Eds.). *Plant cell and tissue culture for the production of food ingredients*, Kluwer Academic/Plenum Publishers, New York, 290 pp, each of which is specifically incorporated herein by reference in its entirety.

IV. Methods of Producing Natural Products with Reduced Glucosinolate

Methods of producing natural products, such as a *Brassicaceae* natural product (for example a *Brassica* natural product, such as anthocyanin) with reduced glucosinolate contamination are disclosed herein. In an embodiment, the methods include cultivating a plant callus such as a *Brassicaceae* plant callus (for example a *Brassica* plant callus, such as a *Brassica oleraceae* plant callus), selecting a plant callus with reduced glucosinolate production, cultivating the selected callus in a suspension medium to obtain a suspension cell culture, and recovering the natural product with reduced glucosinolate contamination from the cell culture. In particular examples, the natural product with reduced glucosinolate contamination is anthocyanin (such as red cabbage anthocyanin).

*Brassicaceae* Plants. The methods disclosed herein can be used to produce natural products with reduced glucosinolate contamination from glucosinolate-producing plants, such as plants of the family *Brassicaceae*.

Plants of *Brassicaceae* include the genus *Brassica* including, but are not limited to, *B. carinata* (Abyssinian mustard or Abyssinian cabbage), *B. elongata* (elongated mustard), *B. fruticulosa* (Mediterranean Cabbage), *B. juncea* (such as Indian mustard, brown and leaf mustards, Sarepta mustard), *B. napus* (such as rapeseed, canola, rutabaga), *B. nigra* (black mustard), *B. oleracea* (such as kale, cabbage, broccoli, cauliflower, Brussels sprouts), *B. rapa* (syn *B. campestris*) (such as Chinese cabbage, turnip, rapini), and *B. rupestris* (brown mustard). In particular examples, plants that can be used in the disclosed methods include *B. oleraceae* var. *capitata* f. *rubra* (red cabbage) for example, cultivars Ruby Perfection, Red Acre, Ruby Ball, Mammoth Red Rock, Buscaro, or Cairo.

Plants of *Brassicaceae* that can be used in the disclosed methods also include plants of the genus *Raphanus*, such as *Raphanus sativus* (cultivated radish) and plants of the genus *Armoracia*, such as *Armoracia rusticana*, syn. *Cochlearia armoracia* (horseradish). Additional plants of *Brassicaceae* that can be used in the disclosed methods include plants from other genera of *Brassicaceae*, including, but not limited to *Matthiola, Arabidopsis, Alyssum, Wasabia, Erysimum,* and *Lepidium*.

Culture conditions utilized to generate natural products with reduced glucosinolates. In an example, a plant callus and/or suspension culture is employed to generate natural products with reduced glucosinolates. Plant callus can be obtained from an appropriate plant using art recognized techniques. The plant tissue can be from a variety of sources, including a cotyledon, root, hypocotyl, shoot tip, stem, leaf, or epidermal peel. The callus can be induced from a tissue explant of a plant capable of producing a desired natural product (such as anthocyanins) through in vitro culture in a suitable nutrient medium. For example, the nutrient medium used in the induction step of the formation of the callus ("induction medium") comprises a solid medium. Suitable nutrient media for plant cell culture, such as for induction of callus formation, are well known to one of skill in the art. In a particular example, a callus induction medium includes Murashige and Skoog (MS) salts (e.g., Cat. No. M524, Phytotech, Shawnee Mission, Kans.) and MS vitamins (e.g., Cat. No. M533, Phytotech, Shawnee Mission, Kans.). See, e.g., Murashige and Skoog, *Physiol. Plant* 15:473-497, 1962.

In an example, callus formation is induced by culture on induction medium containing varying concentrations of hormones (for example, 2,4-dichlorophenoxy-acetic acid (2,4-D), 6-benzylaminopurine (BA), or alpha-naphthaleneacetic acid (NAA)). The induction medium may contain about 0-1 mg/L 2,4-D (for example, about 0 mg/L, 0.5 mg/L, or 1 mg/L), about 0-4 mg/L NAA (for example, about 0 mg/L, 0.1 mg/L, 1 mg/L, 2 mg/L, or 4 mg/L), about 0-0.1 mg/L BA (for example, about 0 mg/L, 0.05 mg/L, or 0.1 mg/L), or various combinations of one or more thereof. In a particular example, callus formation is induced by culture on a solid induction medium that includes about 1 mg/L 2,4-dichlorophenoxyacetic acid, about 2 mg/L alpha-naphthaleneacetic acid, and about 0.1 mg/L 6-benzylaminopurine. Glucosinolate production by the resulting calli can be measured and calli with reduced glucosinolate production selected.

In some examples, reduced glucosinolate production is determined by comparing the amount of glucosinolate (for example total glucosinolates or one or more particular glucosinolate) produced by a callus grown on induction medium containing one or more of 2,4-D, NAA, and BA as compared to a control (such as a callus induced on induction medium lacking 2,4-D, NAA, and/or BA or seedlings of the plant from which the callus was derived). Reduced glucosinolate production includes at least about a 10% decrease (such as about 10%, about 20%, about 30%, about 40%, about 50%, about 60%, about 70%, about 80%, about 90%, about 95%, or even about 99% decrease) as compared to a control (such as a callus induced on induction medium lacking 2,4-D, NAA, and/or BA or seedlings of the plant from which the callus was derived). In other examples, reduced glucosinolate production includes a low amount of glucosinolate (such as total glucosinolates or one or more particular glucosinolate), for example, less than about 5 µg/g FCW, for example about 0.01 µg/g FCW to about 5 µg/g FCW, about 0.05 µg/g FCW to about 2.5 µg/g FCW, about 0.05 µg/g FCW to about 1 µg/g FCW, about 0.05 µg/g FCW to about 0.75 µg/g FCW, or about 0.05 µg/g FCW to about 0.5 µg/g FCW total glucosinolate).

Callus and suspension cultures from plants producing natural products with reduced glucosinolates can be established by protocols known in the art. Exemplary protocols are provided in the Examples below. Briefly, although the following specifics may be varied by those skilled in the art, in a representative method, initiation of a cell culture producing the desired natural product with reduced glucosinolates is achieved by setting up callus and suspension cultures from stable, continuous tissue cultures.

Callus and suspensions cultures may produce the desired natural product naturally or spontaneously. However, at times, though the host plant produces the natural product, the callus and/or suspension cultures may not, or may produce the natural product at lower levels than in the host plant. Methods of inducing or increasing the production of a natural product are known to one of skill in the art. For example, cultures can be induced to produce anthocyanins using light irradiation, especially ultraviolet (UV)-B light which is an elicitor of anthocyanin biosynthesis (Reddy et al., 1994, *Plant Physiol.* 105: 1059-1066). Further, as described below, anthocyanin production can be increased by growth of the culture in a suitable medium, such as a medium lacking a nitrogen source.

Suspension cultures can be raised from the callus cultures and maintained in fresh suspension medium (as detailed in the Examples below). Suitable nutrient media for plant cell suspension culture are well known to one of skill in the art. In a particular example, a plant cell suspension medium includes Murashige and Skoog (MS) salts (e.g., Cat. No. M524, Phytotech, Shawnee Mission, Kans.) and Nitsch and Nitsch vitamins (e.g., Cat. No. N608; Phytotech, Shawnee Mission, Kans.). See, e.g., Nitsch and Nitsch, *Science* 163:85-87, 1969. Suspension cultures can be established by aseptically transferring a known mass of cells expressed as packed cell volume (PCV) to fresh medium on a regular schedule, typically at 7-14 day intervals.

Medium for suspension culture ("suspension medium") can be optimized for initiation of suspension culture or for desired characteristics (such as cell texture or natural product production). In some examples, the concentration of hormones (such as 2,4-D, dicamba, NAA, 6-γ-γ-dimethylallyl-aminopurine (2iP), picloram, indole-3-acetic acid (IAA), gibberellic acid (GA), or kinetin) can be varied individually or in combination. In particular examples, the suspension medium may contain about 0-2 mg/L 2,4-D (for example, about 0 about 0 mg/L, 0.005 mg/l, 0.01 mg/L, 0.05 mg/L, or 0.1 mg/L), about 0-2 mg/L dicamba (for example, about 0 mg/L, 1 mg/L, or 2 mg/L), about 0-1 mg/L GA (for example, about 0 mg/L, 0.5 mg/L, or 1 mg/L), about 0-2 mg/L IAA (for example, about 0 mg/L, 1 mg/L, or 2 mg/L), about 0-1 mg/L kinetin (for example, about 0 mg/L, 0.1 mg/L, 0.5 mg/L, or 1 mg/L), about 0-2 mg/L NAA (for example, about 0 mg/L, 0.5 mg/L, 1 mg/L, or 2 mg/L), about 0-2 mg/L picloram (for example about 0 mg/L, 1 mg/L, or 2 mg/L), about 0-0.1 mg/L BA (for example, about 0 mg/L, 0.01 mg/L, 0.02 mg/L, 0.025 mg/L, 0.05 mg/L, or 0.1 mg/L), or various combinations of one or more thereof. In particular examples, the suspension medium includes about 1.5 mg/L 2,4-D.

Methods of measuring glucosinolate production. Methods of measuring or quantitating glucosinolates are well known to those of skill in the art. In one example, glucosinolates (such as total glucosinolate or particular glucosinolates) are measured by mass spectrometry, such as liquid chromatography-mass spectrometry (LC-MS) techniques. An extract (such as an aqueous extract) from a plant, plant callus, or plant cell culture (such as a plant callus with reduced glucosinolate production) is evaluated by LC-MS. Glucosinolates are detected based on molecular weight and retention time. Quantification can be based on an external calibration curve using known concentrations of a glucosinolate (such as sinigrin). See, e.g., Mellon et al., *Anal. Biochem.* 306:83-91, 2002; Song et al., *J. Sci. Food Agriculture* 86:1271-1280, 2006; Rochfort et al., *Phytochem.* 69:1671-1679, 2008.

In another example, glucosinolates (such as total glucosinolate or particular glucosinolates) are measured by hydrolyzing glucosinolates with the enzyme myrosinase and quantifying the amount of glucose released. See, e.g., Heaney and Fenwick, *Zeitschrift Pflanzenzuchtg* 87:89-95, 1981.

V. Methods of Producing Cabbage Anthocyanin with Reduced Glucosinolate

Disclosed herein are methods for producing cabbage anthocyanin with reduced glucosinolate contamination. In an example, cabbage anthocyanin with reduced glucosinolate contamination is produced by cultivating a red cabbage plant callus with reduced glucosinolate production in a first suspension medium to obtain a suspension cell culture, growing the suspension cell culture in a second suspension medium, and recovering the cabbage anthocyanin from the cell culture. In some examples, the second suspension medium lacks a nitrogen source (for example, does not have any added nitrogen source, such as nitrogen added in the form of exogenous ammonium or nitrate). In additional examples, the second suspension medium includes about 3-10% of a sugar (such as about 3-10% sucrose, for example, about 3%, 4%, 5%, 6%, 7%, 8%, 9% or 10% sucrose).

Production of a red cabbage plant callus with reduced glucosinolate production is carried out as described above. In some examples, reduced glucosinolate contamination of the cabbage anthocyanin is determined by comparing the amount of glucosinolate (for example total glucosinolates or one or more particular glucosinolate) in anthocyanin prepared from the red cabbage plant callus or suspension culture as compared to a control (such as anthocyanin prepared from a plant callus or suspension culture of the plant from which the reduced glucosinolate callus was derived). Reduced glucosinolate contamination includes at least about a 10% decrease (such as about 10%, about 20%, about 30%, about 40%, about 50%, about 60%, about 70%, about 80%, about 90%, about 95%, or even about 99% decrease) as compared to a control (such as anthocyanin prepared from a plant callus or suspension culture of the plant from which the reduced glucosinolate callus was derived). In other examples, reduced glucosinolate contamination is determined as less than about 100 mg/L glucosinolate (such as less than about 100 mg/L, about 75 mg/L, about 50 mg/L, about 25 mg/L, about 10 mg/L, about 5 mg/L, about 1 mg/L, or even about 0.1 mg/L) in the anthocyanin preparation. In further examples, reduced glucosinolate contamination includes a ratio of anthocyanin to glucosinolate that is at least about 40:1 (for example, at least about 40:1, at least about 50:1, at least about 60:1, at least about 80:1, at least about 100:1, at least about 200:1, or even more).

Culture conditions utilized to increase anthocyanin production. Medium for suspension culture can be optimized for production of anthocyanin. In some examples, the amount of nitrogen source (for example ammonium nitrate and/or ammonium sulfate) or the amount or type of carbon source (for example glucose, fructose, sucrose, mannitol, or sorbitol) or other components (such as casein or phosphate) can be varied individually or in combination. In particular examples, the suspension medium may contain 0-80 mM nitrogen source (such as about 0 mM, 10 mM, 20 mM, 30 mM, 40 mM, or 80 mM ammonium and/or nitrate), about 3-10% glucose, fructose, sucrose, mannitol or sorbitol (such as about 3%, 4%, 5%, 6%, 7%, 8%, 9%, or 10%), 0.5-10 g/L casein (such as 0.5 g/L, 1 g/L, 5 g/L, or 10 g/L), or various combinations of one or more thereof. In one example, the suspension medium contains about 4% sucrose (for example, medium BO10923). In other examples, the suspension medium may contain reduced phosphate or lack phosphate (such as a medium with no added phosphate; such as medium that contains less than about 10 μM phosphate (such as less than about 1 μM, less than about 100 nM, less than about 1 nM, or less than about 0.1 nM phosphate), or medium that does not contain detectable levels of phosphate, for example by mass spectrometry). In particular examples, the suspension medium is a medium that contains about 8% sucrose and lacks a nitrogen source (for example, medium BO1224) or is a medium that contains about 8% sucrose and lacks both a nitrogen source and added phosphate (for example, medium BO1851). In some examples, the suspension medium also includes 2,4-D (such as about 1-2 mg/L 2,4-D, for example about 1.5 mg/L 2,4-D). Anthocyanin production by the resulting cell culture can be measured and culture conditions with increased or optimal anthocyanin production selected.

Recovery of anthocyanin pigments. Anthocyanins are recovered or extracted from cell cultures prepared by the methods described herein in ways similar to the methods known in the art for extraction of any other anthocyanins. For example, in a representative embodiment, cells are homogenized and extracted with acidified water (0.1% sulfuric acid, pH 3.0). Modifications to the solvent used for extraction include the addition of ethanol or methanol (up to 50% volume/volume) and the use of acetic acid or any other food grade acid to acidify the solvent (instead of sulfuric acid). The cells may be frozen prior to homogenization if storage is required. For example, cells can be frozen in liquid nitrogen and stored at −80° C.

In one example, the cell suspension cultures are homogenized before removing the spent medium, and the resultant homogenate is filtered. The filtered homogenized cell mass can then be extracted with solvent to remove anthocyanins. In another example, the cell culture is filtered to remove the spent medium and solvent added to the remaining cell mass, then the cells are homogenized in the presence of solvent. In an additional example, spent medium is decanted, the solvent is added to the remaining cell mass, cells are homogenized, and anthocyanins extracted. In all of the aforementioned examples, anthocyanin extraction with solvent may be repeated several times to extract as much anthocyanins as possible from the cell mass.

Methods of measuring anthocyanin production. Methods of measuring the amount or quantity of anthocyanin in a preparation are known to one of skill in the art. Anthocyanin content of a preparation (such as an extract of a cell culture) can be tested for its absorbance at 520 nm and anthocyanin content calculated using Beer's law (A520 nm×1000×MW of cyanidin glucoside)/(extinction coefficient).

The amounts and types of anthocyanins found in a preparation can be determined by LC-MS and by UV absorbance. In some examples, a preparation is subjected to LC-MS analysis. The samples are monitored at 520 nm. Total anthocyanin concentration of an unknown extract can then be expressed as cyanidin-3,5-diglucoside equivalents by summing the peak areas at 520 nm and comparing to a standard curve.

Uses of the anthocyanin preparations. Anthocyanins are extensively used as natural color additives in many food products such as soft drinks, beverages and yogurts. However, anthocyanins produced conventionally, such as extraction from plants such as red cabbage often have undesirable odor and/or taste, which is a result of the presence of glucosinolates in the preparation. Thus, by the methods described herein it is possible to produce anthocyanin with reduced glucosinolate contamination that lacks the undesirable odor and/or taste of current preparations. The anthocyanins produced by the disclosed methods may be used in any food, beverage, drug, cosmetic, or other preparation in place of conventionally prepared anthocyanins.

The following examples are provided to illustrate certain particular features and/or embodiments. These examples should not be construed to limit the disclosure to the particular features or embodiments described.

EXAMPLES

Example 1

Selection of Low Glucosinolate-Producing Red Cabbage Cell Lines

This example describes the selection of red cabbage cell lines which produce low amounts or no glucosinolates.

Thirty seeds of seven different cultivars of Red cabbage (*Brassica oleracea*); Ruby Perfection, Red Acre, Ruby Ball, Mammoth Red Rock, Buscaro, and Cairo, were each put into a 50 mL tube and 30-40 mL of 25% bleach containing 1 drop of Tween-20 per 100 mL of bleach solution was added to the tube. The tube was agitated on a LabQuake® shaker (ThermoScientific, Waltham, Mass.) for 15 minutes. Seeds and bleach were poured through a sterile tea strainer. The seeds were then rinsed three times with sterile water and plated on germination medium (BO254, Table 1) based on MS salts including MS vitamins, 30 g/L sucrose and 2.0 g/L Phytagel™. After 3 weeks, germinated seedlings were cut with a scalpel into three parts (cotyledon, hypocotyls, and root) and transferred by sterile forceps onto callus induction media based on MS salts, MS vitamins, 30 g/L sucrose and 2.0 g/L Phytagel™ with various concentrations of hormones, 2,4-dichlorophenoxyacetic acid (2,4-D), alpha-naphthaleneacetic acid (NAA) and 6-benzylaminopurine (BA) (Media BO278, BO279, BO280, BO281, BO282, BO283; Table 1). After 2-3 weeks, callus was successfully induced and some subcultures eventually gained a better growth rate. Well-growing calli were transferred onto MS medium with 2.0 mg/L NAA, 1.0 mg/L 2,4-D, 0.1 mg/L BA, MS vitamins, 30 g/L sucrose, and 2.0 g/L Phytagel™ (BO283, Table 1).

TABLE 1

Growth media for selection of low glucosinolate cell lines*

|  | B0254 I | B0278 II | B0279 III | B0280 IV | B0281 V | B0282 VI | B0283 VII |
|---|---|---|---|---|---|---|---|
| MS Salts (Phytotech Catalog # M524) (g/L) | 4.33 | 4.33 | 4.33 | 4.33 | 4.33 | 4.33 | 4.33 |
| MS Vitamins 1000X Stock Solution (Phytotech Catalog # M533) (mL/L) | 1.0 | 1.0 | 1.0 | 1.0 | 1.0 | 1.0 | 1.0 |
| 2,4-D (mg/L) |  | 1.0 | 1.0 |  |  | 1.0 | 1.0 |
| NAA (mg/L) |  |  |  | 2.0 | 4.0 | 2.0 | 2.0 |
| BA (mg/L) |  |  | 0.1 |  | 0.1 |  | 0.1 |
| Sucrose (g/L) | 30.0 | 30.0 | 30.0 | 30.0 | 30.0 | 30.0 | 30.0 |
| Phytagel (g/L) | 2.0 | 2.0 | 2.0 | 2.0 | 2.0 | 2.0 | 2.0 |

*Premix salts and vitamins prepared and added per manufacturer's instructions

Figure 1B:
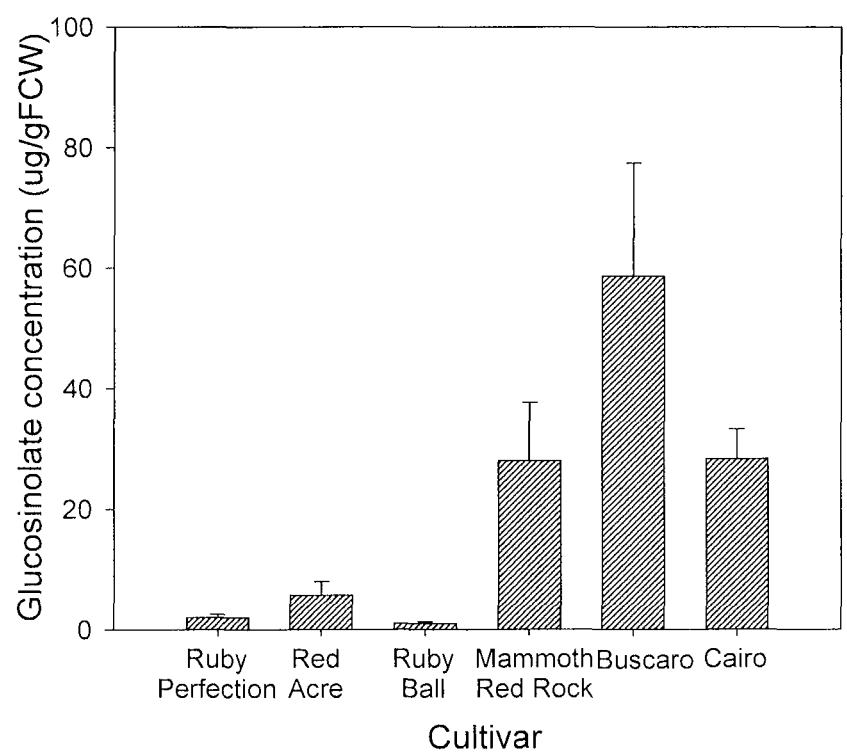

Total glucosinolate levels from the seven different cultivars' stem and petiole-derived calli were evaluated using liquid chromatography-mass spectrometry (FIGS. 1A and 1B, respectively). An extract was prepared from approximately 0.5 mL fresh calli or suspended cells with 1.0 mL 50% (v/v) ethanol including 0.05% $H_2SO_4$. The cells were collected in a microcentrifuge tube (2.0 mL) and homogenized with a bead mill homogenizer for 2 minutes. The homogenates were centrifuged in a clinical centrifuge at 4000 rpm for 4 minutes. 10 µl of the sample was injected to LC-MS analysis. A Symmetry C18 column (100×2.1 mm i.d., 3.5 µm) with a Symmetry C18 10×2.1 mm guard column (Waters, Milford, Mass., USA) was used. LC analyses were performed using a Waters (Milford, Mass., USA) high pressure liquid chromatography (HPLC) system equipped with a CTC Analytics PAL autosampler (Leap Technologies, Carrboro, N.C., USA), Waters 626 pump with 600S Controller and a Waters 996 photodiode-array detector (PDA) scanning from 190 to 780 nm from 0-27 minutes. Gradient elution was carried out with water-0.1% formic acid (solvent A) and acetonitrile-0.1% formic acid (solvent B) at a constant flow-rate of 0.3 mL min$^{-1}$. A linear gradient profile with the following proportions (v/v) of solvent B was applied (t (min), % B): (0, 8), (15, 45), (15.1, 100), (25, 100), (25.1, 8), (35, 8). A Waters Quattro Micro triple-quadrupole mass detector (Milford, Mass., USA) was used simultaneously to obtain the MS data. Mass Spec conditions were: ES negative mode, Capillary voltage 2.95 kV, Cone voltage 15 V, Source temperature 115° C., Desolvation temperature 225° C., Cone gas flow 0 L/hr, Desolvation gas flow 600 L/hr, Ion energy 1, Entrance 50, Collision 2, Exit 50.

Glucosinolate detection was based on molecular weight using ES negative mode scan from 150-1000 m/z. Quantification was based on an external calibration curve using Sinigrin (Sigma-Aldrich, St. Louis, Mo.) at 15.625 µg/mL, 31.25 µg/mL, 62.5 µg/mL, 125 µg/mL and 250 µg/mL. Compounds were detected based on molecular weight and retention time from ES negative mode scan. Detection and quantification of each glucosinolate compound in the extract was based on molecular weight and retention time information (Table 2). Four glucosinolate compounds including glucobrassicin, neoglucobrassicin, 4-methoxyglucobrassicin and 4-hydroxyglucobrassicin were detected and there was significant variation in glucosinolate content among cultivars.

TABLE 2

Molecular weight and retention time of exemplary glucosinolates

| Compound | Molecular weight (Da) | Retention time (+/−2 min) |
|---|---|---|
| Sinigrin | 358 | 2 |
| Glucobrassicanapin | 386 | 7 |
| Neoglucobrassicin | 477 | 14.1 |
| 4-methoxyglucobrassicin | 477 | 11.7 |
| Glucobrassicin | 447 | 7 |
| Glucoerucin | 420 | 8 |
| Gluconapin | 372 | 3.8 |
| 4-hydroxyglucobrassicin | 463 | 6.5 |
| Glucoraphanin | 436 | 8 |

Calli from all red cabbage varieties having low or no glucosinolate content were identified. Total glucosinolate concentrations averaged between 0.06-76.54 µg/g fresh cell weight (FCW) compared to 150-300 µg/g FCW from seedlings of the corresponding varieties. Calli of Ruby Ball (0.06-0.5 µg glucosinolate per gram FCW) displayed exceptionally low levels. Thus, Ruby Ball calli were chosen as low glucosinolate producing cell lines and they showed consistently lower level of glucosinolate production. Nineteen independent calli derived from Ruby Ball cabbage were selected and designated MX797-1 to MX797-19.

Example 2

Optimization of Suspension Culture of Cabbage Cells and Production of Anthocyanin This example describes selection of media for growth of cabbage cell suspension cultures in optimization of production of anthocyanins.

For collecting only the pigmented friable cells, healthy calli of Ruby Ball (Cell lines MX797-5, -6, -8, -9, -11, -12, -13, -14, -15, and -17) growing on BO283 plates as described in Example 1 were transferred onto modified medium based on MS salts including NN vitamins, 30 g/L sucrose and 2.5 g/L Phytagel™ with 1.5 mg/L 2,4-D (BO1168, Table 3). The pH of the medium was adjusted to 5.8 before autoclaving at 1.04 kg/cm$^2$ pressure (121° C.) for 25 minutes. The re-plated red cabbage calli on BO1168 medium demonstrated much better growth and pigmentation. Cell texture also turned more friable, which was adequate for suspension culture creation and propagation. Every 4 weeks, calli were subcultured on the same medium and only dark purple-colored friable calli were transferred on fresh media every subculture time.

TABLE 3

Media for optimization of anthocyanin production*

| Component | BO1155 | BO1168 | BO1224 | DC1151 | BO1851 | BO1293 |
|---|---|---|---|---|---|---|
| MS Salts (Phytotech Catalog # M524) (g/L) | 4.3 | 4.3 | | 4.3 | | 4.3 |
| MS Modified Basal Salt Mixture (Phytotech Catalog #M531) (g/L) | | | 0.78 | | | |
| MS Modified Basal Salt Mixture (Phytotech Catalog #M407) (g/L) | | | | | 0.61 | |
| NN Vitamins (1000X Stock Solution of Phytotech Catalog # N608) (mL/L) | 1.0 | 1.0 | 1.0 | 1.0 | 1.0 | 1.0 |
| 2,4-D (mg/L) | 1.5 | 1.5 | 1.5 | 1.5 | 1.5 | 1.5 |
| Sucrose (g/L) | 80.0 | 30.0 | 80.0 | 30.0 | 80.0 | 40.0 |
| Phytagel (g/L) | | 2.5 | | | | |

*Premix salts and vitamins prepared and added as per manufacturer's instructions After two times subculturing on the solid plate, suspension culture creation was initiated again in MS medium with NN vitamins, 30 g/L sucrose and 1.5 mg/L 2,4-D (DC1151, Table 3). The suspended cells were maintained by subculturing in 30 mL of fresh DC1151 Medium (inoculation size=25% PCV (packed cell volume)) in 125 mL Erlenmeyer flasks. The pH of the medium was adjusted to 5.4 before autoclaving. The cultures were incubated at 23° C. and 115 rpm under 60 µM/m$^2$/sec white fluorescent light (16 hours photo period/day).

At day 6, samples were taken from all the flasks and their anthocyanin production yield was measured by UV absorbance method. Briefly, anthocyanin was extracted from approximately 0.5 mL fresh calli or suspended cells with 1.0 mL 50% (v/v) ethanol including 0.05% H$_2$SO$_4$. The cells were collected in a microcentrifuge tube (2.0 mL) and homogenized with a bead mill homogenizer for 2 minutes. The homogenates were centrifuged in a clinical centrifuge at 4000 rpm for 4 minutes. This extract was diluted 5 times with pH 3.0 buffer solution and tested for its absorbance at 520 nm. Anthocyanin content was calculated using Beer's law (A520 nm×1000×MW of cyanidin glucoside)/(extinction coefficient). At this time the cell line MX797-12 was selected due to its superior growth characteristics for further cell selection process to achieve a homogeneously pigmented fine suspension for productivity optimization and scale-up.

Figure 2:
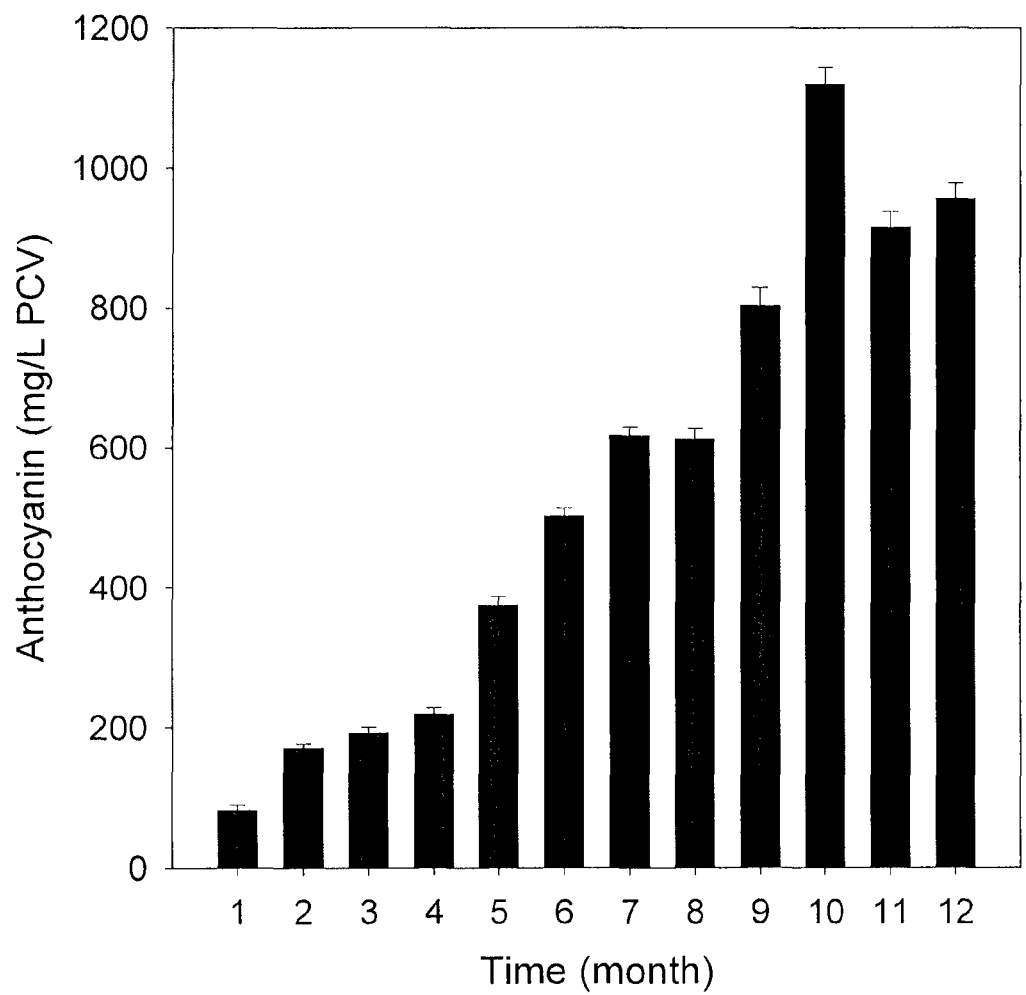
FIG. 2 is a histogram showing anthocyanin production in a representative low-glucosinolate Ruby Ball cabbage suspension cell line, MX797-12, over 12 months in culture.
Figure 3:
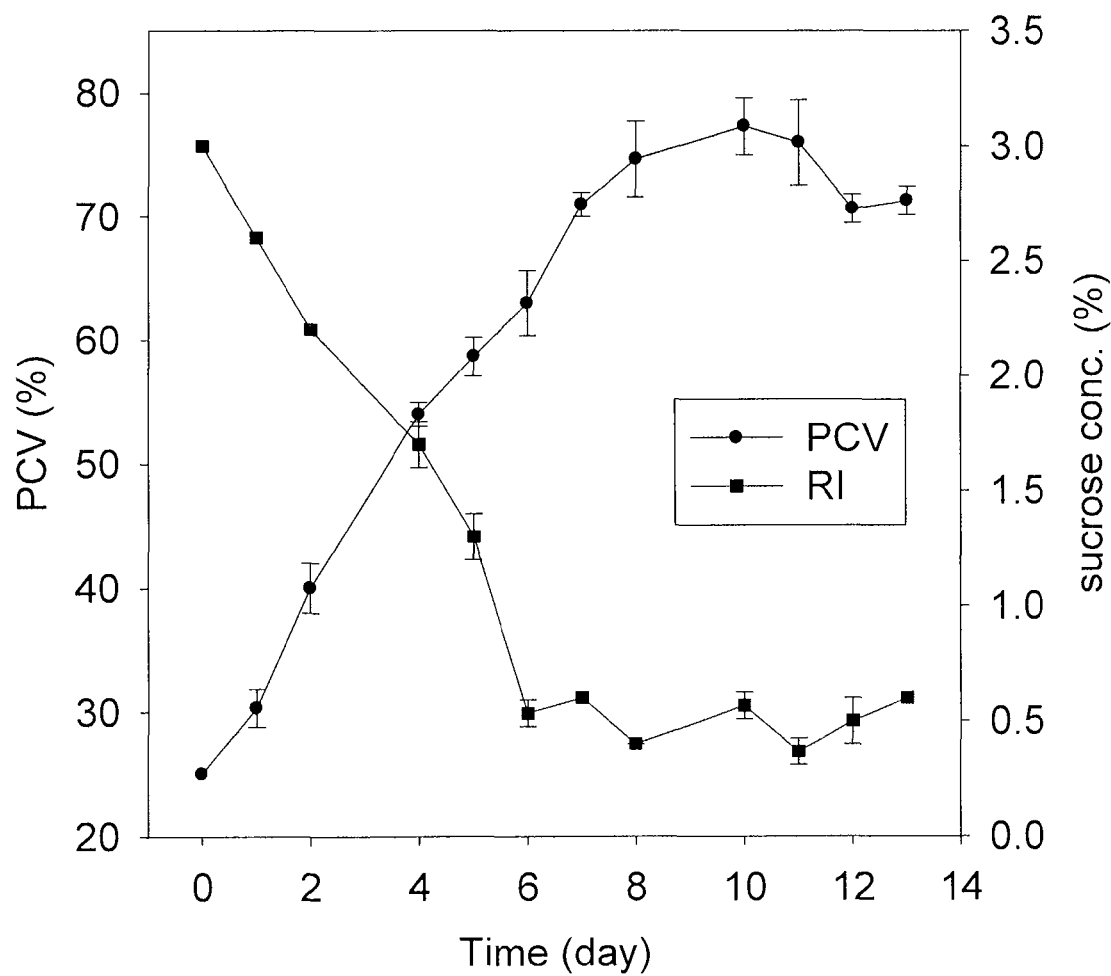
FIG. 3 is a graph showing growth and sucrose consumption patterns of cabbage cell line MX797-12. PCV, packed cell volume; RI, refractive index

Flasks containing high anthocyanin producing cells were selected and 10 mL PCV of cells were transferred to 30 mL of fresh DC1151 Medium to provide 40 mL of culture at 25% (v/v) inoculation density at day 7. After 9 months of selective subculturing, significant improvements of anthocyanin production in 125 mL flask scale were obtained by the regular selection process of high producers and the production was reproducible. Then, the cell culture in 125 mL flasks was scaled-up to 250 mL flask scale. In 250 mL flask scale, 20 mL PCV of cells was transferred to 60 mL of fresh DC1151 medium to provide 80 mL of culture (inoculation density 25% (v/v)). Cell growth and anthocyanin production showed fairly similar patterns in the two different vessel volumes. Continuous cell selection process supported anthocyanin production increase in the maintenance culture and the total amount of anthocyanin produced from MX797-12 cell line was enhanced about 13.6 fold (from 81.9±7.9 mg/L PCV to 1119.0±24.6 mg/L PCV) at maximum by cell selection process for 12 months (FIG. 2). The maximum growth between day 0 and day 7 of MX797-12 cell line as measured by doubling time was 4.8 days (FIG. 3).

To further enhance cell growth and anthocyanin production the maintenance medium was modified to increase sugar concentration. Thus, medium BO1923 was developed which differed from DC1151 in that the sucrose concentration was increased to 4% (40 g/L medium) (Table 3). This change resulted in a 2.3-fold increase of anthocyanin production (1119.0±24.6 mg/L PCV to 2612.5±513.2 mg/L PCV) on average after eight months of growth in BO1923.

In order to evaluate the effect of depletion of nitrogen source, all nitrogen source was removed from BO1155 to create medium BO1224 (Table 3). Spent medium of 7 day old cultures was replaced with BO1224. This medium demonstrated that anthocyanin production went up to about 2060 mg/L of PCV, indicating that nitrogen source depletion improved anthocyanin production with a higher concentration of sucrose.

Example 3

Optimization of Anthocyanin Production in Cabbage Suspension Cells Using Sucrose This example describes the effect of initial sucrose concentration and supplemental sucrose addition on anthocyanin production.

The productivity of anthocyanin in a suspension culture of MX797-12 was monitored after the addition of sucrose. 20 mL of 7 day old cell culture was inoculated into a 250 mL flask containing 60 mL of DC1151 medium including 3%, 4%, 5% or 6% (w/v) sucrose as initial sucrose concentration and the cells were allowed to grow for another 7 days, incubated at the same growth condition described in Example 2. Then, using a stock solution of sterile 50% (w/v) sucrose, appropriate amounts were added to each of the cultures to adjust the refractive index (RI) to 5%, and the anthocyanin productivity was compared between the treatments after two days. The flasks that were started on 6% sucrose produced 1408.7±116.5 mg/L PCV anthocyanin on day 9, which was almost 2-fold higher than the productivity of cells started on 3% sucrose (Table 4). Initial sucrose concentration affected anthocyanin production in regular maintenance culture for 7 days as well as production increase from sucrose addition at day 7.

TABLE 4

Cell growth and anthocyanin production after addition of 5% sucrose

| Initial sucrose concentration | % PCV at day 9 | Anthocyanin at day 9 (mg/L PCV) |
| --- | --- | --- |
| 3% | 77.0 ± 1.7 | 711.5 ± 78.0 |
| 4% | 75.0 ± 0.2 | 853.2 ± 102.5 |
| 5% | 75.3 ± 0.6 | 1070.7 ± 162.1 |
| 6% | 75.3 ± 1.5 | 1408.7 ± 116.5 |

Example 4

Effect of Phosphate in Production Medium Development

This example describes the effect of phosphate depletion on anthocyanin production.

In an effort to increase anthocyanin production in the production medium, phosphate was deprived from BO1224 to formulate production medium BO1851 (Table 3). 20 mL PCV of MX797-12 cells were inoculated in 60 mL of fresh DC1151 medium for initial 7 days culture and were inoculated as described in Example 2. At day 7, PCV and RI were measured prior to medium change, which were 59.3±1.4% and 0.54±0.05%, respectively. Spent medium of 7 day old suspensions was replaced with BO1851 without changing the PCV and incubated for another 7 days. The production of anthocyanin was compared with a control flask which contained BO1224 medium. The amount of anthocyanin produced with BO1851 (1369.5±460 mg/L PCV) was 2.2 times higher than the control (Table 5).

TABLE 5

Phosphate effect on cell growth and anthocyanin production.

|  | BO1224 | BO1851 |
| --- | --- | --- |
| PCV (%) | 80.0 ± 0.0 | 76.5 ± 4.9 |
| Anthocyanin (mg/L PCV) | 620.3 ± 19.2 | 1369.5 ± 460 |

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims.

What is claimed is:

1. A method for producing cabbage anthocyanin with less than 100 mg/L glucosinolate contamination in the cabbage anthocyanin, comprising:
   cultivating a red cabbage plant callus with reduced glucosinolate production of at least a 10% decrease as compared to a plant or plant callus from which the red cabbage plant callus was derived in a first suspension medium to obtain a first suspension cell culture with less than 76.54 μg total glucosinolate per gram fresh cell weight;
   growing the first suspension cell culture in a second suspension medium lacking a nitrogen source to obtain a second suspension cell culture with less than 76.54 μg total glucosinolate per gram fresh cell weight and at least 81.9 mg of anthocyanin per liter of packed cells; and
   recovering the cabbage anthocyanin from the second suspension cell culture with less than 76.54 μg total glucosinolate per gram fresh cell weight and at least 81.9 mg of anthocyanin per liter of packed cells.

2. The method of claim 1, wherein cultivating the red cabbage plant callus with reduced glucosinolate production of at least a 10% decrease as compared to a plant or plant callus from which the red cabbage plant callus was derived comprises inducing the formation of the plant callus with reduced glucosinolate production of at least a 10% decrease as compared to a plant or plant callus from which the red cabbage plant callus was derived through in vitro culture in an induction medium.

3. The method of claim 2, wherein the induction medium comprises 2,4-dichlorophenoxyacetic acid, alpha-naphthaleneacetic acid, and 6-benzylaminopurine.

4. The method of claim 3, wherein the induction medium comprises about 1 mg/L 2,4-dichlorophenoxyacetic acid, about 2 mg/L alpha-naphthaleneacetic acid, and about 0.1 mg/L 6-benzylaminopurine.

5. The method of claim 1, wherein the second suspension medium comprises about 3% to 8% sucrose (weight/volume).

6. The method of claim 5, wherein the second suspension medium does not contain added phosphate.

7. The method of claim 1, wherein the red cabbage plant callus with reduced glucosinolate production of at least a 10% decrease as compared to a plant or plant callus from which the red cabbage plant callus was derived is a *Brassica oleracea* var. *capitata* f. *rubra* plant callus with reduced glucosinolate production of at least a 10% decrease as compared to a *Brassica oleracea* var. *capitata* f. *rubra* plant or plant callus from which the *Brassica oleracea* var. *capitata* f. *rubra* plant callus was derived.

8. The method of claim 7, wherein the *Brassica oleracea* var. *capitata* f. *rubra* plant callus is of cultivar Ruby Perfection, Red Acre, Ruby Ball, Mammoth Red Rock, Buscaro, or Cairo.

9. A method for producing cabbage anthocyanin with less than 100 mg/L glucosinolate contamination in the cabbage anthocyanin, comprising:
cultivating a red cabbage plant callus with reduced glucosinolate production of at least a 10% decrease as compared to a plant or plant callus from which the red cabbage plant callus was derived in a first suspension medium to obtain a first suspension cell culture;
growing the first suspension cell culture in a second suspension medium having an initial sucrose concentration of about 3-8% sucrose (w/v) to obtain a second suspension cell culture; and
recovering the cabbage anthocyanin from the second suspension cell culture, thereby producing cabbage anthocyanin with less than 100 mg/L glucosinolate contamination in the cabbage anthocyanin,
wherein the ratio of anthocyanin to glucosinolate in the recovered cabbage anthocyanin is at least 40:1.

10. The method of claim 9, wherein the second suspension medium has an initial sucrose concentration of about 6% sucrose (w/v).

11. The method of claim 1, wherein the cultivated red cabbage plant callus has reduced glucosinolate production of at least a 90% decrease as compared to a plant or plant callus from which the red cabbage plant callus was derived.

12. The method of claim 1, wherein the recovered cabbage anthocyanin has less than 100 mg/L glucosinolate contamination and a ratio of anthocyanin to glucosinolate in the recovered cabbage anthocyanin is at least 40:1.

13. The method of claim 1, wherein the recovered cabbage anthocyanin has a ratio of anthocyanin to glucosinolate that is at least 100:1.

14. The method of claim 13, wherein the recovered cabbage anthocyanin has less than 10 mg/L glucosinolate contamination.

15. The method of claim 9, wherein the first suspension cell culture comprises less than 76.54 µg total glucosinolate per gram fresh cell weight.

16. The method of claim 9, wherein the second suspension cell culture comprises less than 76.54 µg total glucosinolate per gram fresh cell weight and at least 81.9 mg of anthocyanin per liter of packed cells.

17. A method for producing a *Brassica* natural product preparation with anthocyanin and reduced glucosinolate contamination, comprising:
cultivating *Brassica* plant callus;
growing a plurality of calli from the cultivated *Brassica* plant callus;
selecting from the plurality of calli a *Brassica* plant callus with reduced glucosinolate production of at least a 10% decrease as compared to the cultivated *Brassica* plant callus;
cultivating the selected *Brassica* plant callus in a first suspension medium to obtain a suspension cell culture with less than 76.54 µg total glucosinolate per gram fresh cell weight and at least 81.9 mg of anthocyanin per liter of packed cells; and
recovering *Brassica* natural product from the suspension cell culture, wherein the recovered *Brassica* natural product comprises anthocyanin, wherein the ratio of anthocyanin to glucosinolate in the recovered *Brassica* natural product is at least 40:1.

18. The method of claim 16, wherein the recovered *Brassica* natural product has less than 100 mg/L glucosinolate contamination and a ratio of anthocyanin to glucosinolate in the recovered cabbage anthocyanin is at least 40:1.

19. The method of claim 16, wherein the recovered *Brassica* natural product comprises anthocyanin and has less than 10 mg/L glucosinolate contamination, wherein the ratio of anthocyanin to glucosinolate in the recovered *Brassica* natural product is at least 100:1.

20. The method of claim 16, wherein the selected *Brassica* plant callus produces 0.06 to 76.54 µg total glucosinolate per gram fresh cell weight.

* * * * *